United States Patent
Cabral-Lilly et al.

(10) Patent No.: US 10,166,184 B2
(45) Date of Patent: *Jan. 1, 2019

(54) METHOD OF LYOPHILIZING LIPOSOMES

(71) Applicant: CELATOR PHARMACEUTICALS INC., Ewing, NJ (US)

(72) Inventors: Donna Cabral-Lilly, Pennington, NJ (US); Lawrence Mayer, North Vancouver (CA); Paul Tardi, Surrey (CA); David Watkins, East Greenwich, RI (US); Yi Zeng, Somerset, NJ (US)

(73) Assignee: CELATOR PHARMACEUTICALS INC., Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,170

(22) Filed: Feb. 7, 2018

(65) Prior Publication Data

US 2018/0161273 A1    Jun. 14, 2018

Related U.S. Application Data

(63) Continuation of application No. 14/352,662, filed as application No. PCT/US2012/060293 on Oct. 15, 2012, now Pat. No. 10,028,912.

(Continued)

(51) Int. Cl.
| | |
|---|---|
| A61K 9/127 | (2006.01) |
| A61K 45/06 | (2006.01) |
| A61K 47/26 | (2006.01) |
| A61K 9/19 | (2006.01) |
| A61K 31/4745 | (2006.01) |
| A61K 31/704 | (2006.01) |
| A61K 31/7068 | (2006.01) |
| A61K 31/7072 | (2006.01) |

(52) U.S. Cl.
CPC ............ *A61K 9/127* (2013.01); *A61K 9/1277* (2013.01); *A61K 9/19* (2013.01); *A61K 31/4745* (2013.01); *A61K 31/704* (2013.01); *A61K 31/7068* (2013.01); *A61K 31/7072* (2013.01); *A61K 45/06* (2013.01); *A61K 47/26* (2013.01)

(58) Field of Classification Search
CPC .................................................... A61K 9/127
See application file for complete search history.

(56) References Cited

U.S. PATENT DOCUMENTS

| | | | |
|---|---|---|---|
| 4,883,665 A | 11/1989 | Miyazima et al. | |
| 4,915,951 A | 4/1990 | Baldeschwieler et al. | |

(Continued)

FOREIGN PATENT DOCUMENTS

| | | |
|---|---|---|
| JP | 62-501631 | 7/1987 |
| JP | 2001-519776 | 10/2001 |

(Continued)

OTHER PUBLICATIONS

Bendas et al., "Synthetic glycolipids as membrane-bound cryoprotectants in the freeze-drying process of liposomes," Eur J Pharm Sci (1996) 4:211-222.

(Continued)

*Primary Examiner* — Gollamudi Kishore
(74) *Attorney, Agent, or Firm* — Morrison & Foerster LLP

(57) ABSTRACT

Lyophilized liposomal formulations with two or more encapsulated drugs are disclosed. These formulations display superior drug retention profiles and also maintain size distribution following lyophilization and reconstitution.

17 Claims, 6 Drawing Sheets

Related U.S. Application Data

(60) Provisional application No. 61/550,047, filed on Oct. 21, 2011.

(56) References Cited

U.S. PATENT DOCUMENTS

| | | | |
|---|---|---|---|
| 4,927,571 | A | 5/1990 | Huang et al. |
| 5,077,056 | A | 12/1991 | Bally et al. |
| 5,817,334 | A | 10/1998 | Schmidt |
| 6,319,517 | B1 | 11/2001 | Cavallo et al. |
| 7,850,990 | B2 | 12/2010 | Tardi et al. |
| 8,022,279 | B2 | 9/2011 | Mayer et al. |
| 8,092,828 | B2 | 1/2012 | Louie |
| 2004/0247660 | A1 | 12/2004 | Singh |
| 2006/0110441 | A1 | 5/2006 | Wong et al. |
| 2011/0002982 | A1 | 1/2011 | Tardi et al. |

FOREIGN PATENT DOCUMENTS

| | | |
|---|---|---|
| JP | 2005-509000 | 4/2005 |
| JP | 2006-523713 | 10/2006 |
| JP | 2007-533670 | 11/2007 |
| WO | WO-86/03938 | 7/1986 |
| WO | WO-97/29782 | 8/1997 |
| WO | WO-98/36736 | 8/1998 |
| WO | WO-99/65465 | 12/1999 |
| WO | WO-01/05372 | 1/2001 |
| WO | WO-03/041681 | 5/2003 |
| WO | WO-2004/093795 | 11/2004 |
| WO | WO-2005/102359 | 11/2005 |
| WO | WO-2007/050784 | 5/2007 |
| WO | WO-2008/101214 | 8/2008 |
| WO | WO-2009/070761 | 6/2009 |
| WO | WO-2009/097011 | 8/2009 |
| WO | WO-2010/043050 | 4/2010 |
| WO | WO-2011/092708 | 8/2011 |

OTHER PUBLICATIONS

Communication pursuant to Article 94(3) EPC for EP 12 841 616.1, dated Jan. 20, 2017, 5 pages.
Dos Santos et al., "Improved retention of idarubicin after intravenous injection obtained for cholesterol-free liposomes," Biochim Biophys Acta (2002) 1561(2):188-201.
Goodrich et al., "Alterations in membrane surfaces induced by attachment of carbohydrates," Biochem (1991) 30(21):5313-5318.
International Preliminary Report on Patentability and Written Opinion for PCT/US2012/060293, dated Apr. 22, 2014, 10 pages.
International Search Report for PCT/US2012/60293, dated Jan. 18, 2013, 3 pages.
Notice of Reason(s) for Rejection (including translation) for JP 2014-537142, dated Oct. 11, 2016, 11 pages.
Joguparthi et al., "Liposome Transport of Hydrophobic Drugs: Gel Phase Lipid Bilayer Permeability and Partitioning of the Lactone Form of a Hydrophobic Camptothecin, DB-67," Journal of Pharmaceutical Sciences (2008) 97(1):400-420.
Supplementary European Search Report for EP 12841616.1, dated Mar. 25, 2015, 6 pages.
Tardi et al., Biochimica et Biophysica Acta (2007) 1768:678-687.

Lyophilized CPX-1
Menu File: C370. TBL 1/4/80

Volume-Weighted Gaussian Analysis (Vesicles)

Gaussian Summary:

Mean Diameter = 116.5 nm          Chi Squared    = 0.161
Stnd. Deviation = 27.8 nm (23. 8 %)   Baseline Adj.  = 0.046 %
Coeff. of Var' n = 0.238           Mean Diff. Coeff. = 3.94E-08 $cm^2$/s

| Diameter (nanometers) | Volume: Relative | Percent |
|---|---|---|
| 27.7 | 0.000 | 0.000 |
| 31.9 | 0.000 | 0.000 |
| 36.9 | 0.000 | 0.000 |
| 42.6 | 0.000 | 0.005 |
| 49.2 | 0.002 | 0.053 |
| 56.8 | 0.015 | 0.364 |
| 65.6 | 0.073 | 1.744 |
| 75.8 | 0.243 | 5.801 |
| 87.5 | 0.560 | 13.396 |
| 101.0 | 0.898 | 21.478 |
| 116.7 | 1.000 | 23.911 |
| 134.7 | 0.773 | 18.482 |
| 155.6 | 0.415 | 9.919 |
| 179.6 | 0.155 | 3.696 |
| 207.5 | 0.040 | 0.956 |
| 239.6 | 0.007 | 0.172 |
| 276.6 | 0.001 | 0.021 |
| 319.5 | 0.000 | 0.002 |
| 368.9 | 0.000 | 0.000 |
| 426.0 | 0.000 | 0.000 |

Cumulative Results:

25 % of Distribution <  89.64 nm
50 % of Distribution < 105.47 nm
75 % of Distribution < 124.40 nm
90 % of Distribution < 144.36 nm
99 % of Distribution < 183.79 nm Run Time      = 0 Hr 4 Min 56 Sec    Wavelength  = 632.8 nm
Count Rate    = 360 KHz              Temperature = 23 deg C
Channel #1    = 256.8 K              Viscosity   = 0.945 cp
Channel Width = 13.0 uSec            Index of Ref. = 1.335

FIG. 2

Menu File : C370. TBL 1/4/80

Volume-Weighted Gaussian Analysis (Vesicles)

Gaussian Summary:

Mean Diameter = 116.9 nm  
Stnd. Deviation = 37.9 nm (32.4 %)  
Coeff. of Var' n = 0.324

Chi Squared = 0.204  
Baseline Adj. = 0.009 %  
Mean Diff. Coeff. = 3.92E-08 $cm^2/s$

| Diameter (nanometers) | Volume: Relative | Percent |
|---|---|---|
| 15.6 | 0.000 | 0.000 |
| 18.0 | 0.000 | 0.000 |
| 20.8 | 0.000 | 0.000 |
| 24.0 | 0.000 | 0.000 |
| 27.7 | 0.000 | 0.002 |
| 32.0 | 0.001 | 0.011 |
| 36.9 | 0.003 | 0.055 |
| 42.6 | 0.013 | 0.225 |
| 49.2 | 0.043 | 0.757 |
| 56.8 | 0.120 | 2.094 |
| 65.6 | 0.271 | 4.754 |
| 75.8 | 0.506 | 8.858 |
| 87.5 | 0.773 | 13.547 |
| 101.0 | 0.971 | 17.004 |
| 116.7 | 1.000 | 17.518 |
| 134.7 | 0.846 | 14.813 |
| 155.6 | 0.587 | 10.280 |
| 179.7 | 0.334 | 5.856 |
| 207.5 | 0.156 | 2.738 |
| 239.6 | 0.060 | 1.051 |
| 276.7 | 0.019 | 0.331 |
| 319.5 | 0.005 | 0.086 |
| 369.0 | 0.001 | 0.018 |
| 426.1 | 0.000 | 0.003 |
| 492.1 | 0.000 | 0.000 |
| 568.2 | 0.000 | 0.000 |
| 656.2 | 0.000 | 0.000 |

Cumulative Results:

25 % of Distribution < 82.71 nm  
50 % of Distribution < 103.31 nm  
75 % of Distribution < 128.81 nm  
90 % of Distribution < 155.92 nm  
99 % of Distribution < 221.87 nm Run Time = 0 Hr 21 Min 0 Sec  
Count Rate = 358 KHz  
Channel #1 = 1202.9 K  
Channel Width = 14.0 uSec Wavelength = 632.8 nm  
Temperature = 23 deg C  
Viscosity = 0.945 cp  
Index of Ref. = 1.335

FIG. 3

METHOD OF LYOPHILIZING LIPOSOMES

CROSS-REFERENCE TO RELATED APPLICATIONS

This application is a continuation of U.S. application Ser. No. 14/352,662 having an international filing date of 15 Oct. 2012, which is the national phase of PCT application PCT/US2012/060293 having an international filing date of 15 Oct. 2012, which claims benefit of U.S. provisional patent application No. 61/550,047 filed 21 Oct. 2011. The contents of the above patent applications are incorporated by reference herein in their entirety.

TECHNICAL FIELD

The invention relates to compositions and methods for producing lyophilized liposomes that contain at least two therapeutic or diagnostic agents that can be stored for prolonged periods of time. In one aspect, the invention concerns low-cholesterol liposomes optionally in an external medium comprising a cryoprotectant having resistance to freeze/thaw and dehydration damage of the liposomes thus preserving their size and integrity.

BACKGROUND OF THE INVENTION

Liposomes are closed vesicles having at least one lipid bilayer surrounding an aqueous core. The intra-liposomal space and lipid layer(s) can entrap a wide variety of substances including drugs, cosmetics, diagnostic reagents, genetic material and bioactive compounds. Since non-toxic lipids act as the basis for liposomes, they generally exhibit low toxicity. The low toxicity coupled with the ability of liposomes to increase the plasma circulation lifetime of agents gives rise to liposomes as vehicles particularly useful for delivering pharmaceutically active agents. In many cases, liposome-delivered drugs result in superior clinical efficacy paired with reduced toxicity.

The practical application of liposomal preparations as drug delivery vehicles is limited by the chemical and physical stability of the preparation. Commercialization requires long term stability at both the chemical and physical levels. The use of frozen or freeze-dried (lyophilized) preparations to avoid breakdown of labile drug and/or lipid components provides some improvement in stability. However, during the lyophilization process, ice crystal formation can lead to mechanical rupture, liposome aggregation and fusion (resulting in increased liposome size). Moreover, when liposomes containing drug are lyophilized and then reconstituted at room temperature, changes often occur in the structure of their bilayer(s) which gives rise to accelerated drug leakage.

Prior attempts at preparing lyophilized liposomal compositions have relied on conventional liposomes which are typically in a liquid phase at body temperature where movement of the lipids is fluid and uncontrolled. Such conventional liposomes fall into two categories. The first are maintained in a liquid state because they comprise lipids wherein the gel-to-liquid crystalline temperature ($T_c$) is below body temperature (i.e., they will be in the liquid phase at body temperature). These liposomes are routinely used in the art however; the downside of being fluid is poor drug retention for many encapsulated agents.

The second type of conventional liposomes never undergo a liquid to gel transition because they include high amounts of membrane rigidification agents, such as cholesterol (e.g., 30-45 mol %). Cholesterol acts to increase bilayer thickness and fluidity while decreasing membrane permeability, protein interactions, and lipoprotein destabilization of the liposome. These high amounts of cholesterol are most frequently used in liposomal studies and historically have been taught as necessary for adequate serum stability and drug retention in vivo, though not all drugs can be sufficiently retained. Certain drugs exhibit better drug retention both in vitro and in vivo in liposomes containing substantially no cholesterol. See, e.g., Dos Santos, et al., *Biochim. Biophs. Acta*, (2002) 1561:188-201.

On the other hand, liposomes in the gel-phase are more stable and exhibit improved drug retention. The invention takes advantage of liposomes which are in the gel phase at body temperature (i.e., body temperature is below the $T_c$ of the liposomes). Gel-phase liposomes can be prepared with a number of lipids; however, those made with more saturated acyl side chain phosphatidyl lipids, such hydrogenated soy PC, dipalmitoyl phosphatidylcholine (DPPC) or distearoyl phosphatidylcholine (DSPC) are required to have less than 30% cholesterol in order to achieve gel-phases at body temperature. One example of conventional liposomes that do not exhibit gel-phases at body temperature are those made of egg phosphatidylcholine (EPC) which are significantly leaky.

Prior attempts at preparing lyophilized liposomal compositions using conventional liposomes have involved either empty liposomes or liposomes containing only a single agent. They may employ a cryoprotectant, typically a saccharide, both inside and outside of the liposomes or a large osmotic gradient across the liposomal membrane.

For example, cryoprotectants were used to protect against freeze/thaw damage to 'liquid' EPC liposomes encapsulating a single agent when present in sufficient amounts both on the inside and outside of the liposomes, ideally when these amounts are equal. See, e.g., U.S. Pat. Nos. 5,077,056 and 4,883,665. The presence of 1%-10% cryoprotectant in the internal liposomal medium preserves a lyophilized EPC liposome-encapsulated doxorubicin formulation where preferably the internal osmolarity is near physiological osmolarity. See, e.g., U.S. Pat. No. 4,927,571. Failure to include a cryoprotectant in the liposome interior has been shown to result in a loss of liposome integrity upon reconstitution, particularly with regard to retaining an encapsulated agent. As described, "prevention of leakage requires the sugar be present both inside and outside the liposome" (Lowery, M. (June 2002) *Drug Development and Delivery*, Vol. 2, No. 4).

In one case, protection from vesicle aggregation and fusion, as well as against loss of an entrapped drug, has also been reported for hydrogenated soy PC:cholesterol:DSPE-mPEG (51:44:5 molar ratio) liposomes where the liposome preparation contains 44 mol % cholesterol as well as a cryoprotectant and a high concentration of salt in the external medium. The presence of 44% cholesterol means that the liposomes will be in the liquid phase at or below body temperature. Furthermore, the protective effect is only realized if a large osmotic gradient exists across the membrane such that the outer liposome osmolarity is significantly higher than the internal osmolarity. See, e.g., WO01/05372.

Membrane-bound cryoprotectants also further improve resistance to freezing and lyophilizing of these non-gel phase liposomes. In particular, sugars grafted onto EPC or EPC:cholesterol (1:1 molar ratio) liposomal membrane surfaces via oligo (ethylene oxide) linkers consisting of one to three repeating units have been reported to be cryoprotective for liposomes containing a fluorescent probe. See, e.g., Bendas, et al., *Eur. J. Pharm. Sci.* (1996) 4:211-222; Goodrich, et al., *Biochem.* (1991) 30:5313-5318; U.S. Pat.

No. 4,915,951. Baldeschwieler, et al., reported that in the absence of the terminal sugar group, liposomes prepared with the oligoethylene oxide linker itself were unable to protect against fusion subsequent to freezing. U.S. Pat. No. 4,915,951.

Trehalose in the external medium of a PC liposome formulation encapsulating a single agent provides resistance to liposome aggregation and fusion. U.S. Pat. No. 6,319,517. Other methods of producing small liposomes stabilized against aggregation require the formation of empty PC:Cholesterol (1:1 molar ratio) liposomes to which a solution of sugar and a single reagent are added and then subsequently dried. During the drying process a percentage of the reagent is entrapped within the liposome. These liposomes are reportedly more stable upon storage than in the absence of sugar. See, e.g., WO99/65465.

As stated previously, most previous techniques for lyophilization focused on lyophilization of either empty liposomes or liposomes encapsulating a single agent. Lyophilization with retention of integrity is more challenging where two or more agents are encapsulated, especially if the agents differ in solubility characteristics. Encapsulating two or more agents is often useful since many life-threatening diseases such as cancer, are influenced by multiple molecular mechanisms and due to this complexity, achieving cures with a single agent has been met with limited success. Therefore, almost all cancer treatments involve combinations of more than one therapeutic agent. This is true of treatment of other conditions as well, including infections and chronic diseases.

PCT publication WO03/041681, incorporated herein by reference, reports that gel-phase liposomes with transition temperatures of 38° C. or greater can be prepared using saturated phosphatidyl lipids such as DPPC and DSPC and lower amounts (0-20%) of cholesterol if at least 1 mol % of phosphoinositol (PI) or phosphatidylglycerol (PG) are included in the compositions. These liposomes, when containing combinations of encapsulated irinotecan and floxuridine (FUDR) were shown to be stable to freezing at −20° C. Simple freezing is generally less harsh and less destructive to liposome integrity than lyophilization.

The use of liposomes as delivery vehicles for these combinations is advantageous, particularly if the liposomes include, and are capable of maintaining, ratios of the agents that are non-antagonistic. This general approach is described in detail in U.S. Pat. No. 7,850,990, incorporated herein by reference. This patent teaches how to determine non-antagonistic or synergistic ratios of various therapeutic agents, including antineoplastic agents that maintain such non-antagonism or synergy over a wide range of concentrations. The patent also teaches that it is essential to deliver the drugs in the administered ratio and maintaining that ratio by letting delivery vehicles control the pharmacokinetics. Exemplified in this patent are liposomes that contain, and maintain the ratio of, non-antagonistic or synergistic ratios of two or more therapeutic agents, including irinotecan and FUDR. Such combinations encapsulated in liposomes would benefit from the advantages of being stored in lyophilized form if, upon reconstitution, the integrity of the liposomes and the concentration of the agents and their ratios are maintained. A particularly useful such combination of cytarabine and daunorubicin encapsulated in liposomes is described in U.S. Pat. No. 8,022,279, also incorporated herein by reference.

The use of these combinations in therapeutic protocols with surprisingly good results is described in PCT publication WO2007/050784 and PCT publication WO2008/101214. Additional formulations with liposomal encapsulation of desired drug delivery options are described in WO2009/097011 and WO2009/070761, as well as WO2010/043050. These formulations are simply exemplary of useful compositions wherein two or more therapeutic agents are contained in liposomes for delivery to the patient.

As described above, preparing stable lyophilized compositions of liposomes in general that maintain their integrity upon reconstitution has been difficult and unpredictable. Obtaining such stable liposomal compositions for combinations of two or more agents is even more challenging. Thus, the success of the method of the invention in obtaining lyophilized liposomes wherein the liposomes contain two or more therapeutic or diagnostic agents, and wherein they maintain their integrity upon reconstitution, is a remarkable achievement.

DISCLOSURE OF THE INVENTION

It has consistently been reported that a cryoprotectant is required both inside and outside of liposomes in order to maintain liposome integrity upon reconstitution after lyophilization, particularly in order to ensure retention of an encapsulated agent. The present inventors have identified stable liposomes that require no internal cryoprotectant for successful lyophilization of liposomes encapsulating not only one, but two or more active agents.

The invention relates to successful lyophilized gel-phase liposomal preparations that contain more than one therapeutic and/or diagnostic agent and no internal cryoprotectant. Thus, in one aspect, the invention is directed to a lyophilized liposomal composition wherein said liposomes are stably associated with at least two therapeutic and/or diagnostic agents and wherein when said composition is reconstituted, the mean diameter of the liposomes is maintained compared to the pre-lyophilization state and the percentage of each of the agents that remains encapsulated in the liposomes is maintained at a satisfactory level. The integrity of the liposomes is thus measured as the percentage of encapsulated agents retained after reconstitution of the liposomes. An additional parameter used as a criterion for satisfactory lyophilization is minimal change in size distribution. A particularly important embodiment is that wherein the agents are encapsulated inside the liposomes at a defined ratio and wherein the ratio of these agents is maintained when the lyophilized forms are reconstituted.

Typical conditions for achieving this result include the use of gel-phase liposomes with gel-to-liquid crystalline transition temperatures ($T_c$) that are at least room temperature and may be at or above human body temperature. Body temperature is considered to be about 37° C. The liposomes may be low cholesterol liposomes that are stabilized with phosphatidylglycerol and/or phosphoinositol. The liposomes contain substantially no internal cryoprotectant, but may contain external cryoprotectant at their surfaces and thus may be lyophilized in the presence of a medium containing cryoprotectant. The term "substantially no internal cryoprotectant" is meant to include liposomes that comprise no internal cryoprotectant as well as liposomes which contain an amount of cryoprotectant which does not affect the freezing and/or lyophilization process of said liposomes (i.e., 125 mM cryoprotectant or less that is, an "inactive" amount). Therefore "substantially no internal cryoprotectant" is defined to be from about 0-125 mM cryoprotectant inside the liposomes. It is important to note that preventing drug leakage following the lyophilization process is significantly more difficult than retention of liposome size. As mentioned above, drug retention following lyophilization has historically been achieved via the use of a cryoprotectant both on the inside and outside of the liposomes.

Thus, in one embodiment, the liposomes have gel-to-liquid crystalline transition temperatures ($T_c$'s) of the membrane greater than room temperature or greater than 25° C. or 37° C. so that, at least at room temperature, e.g., 25° C., the lipid membrane is sufficiently gel-like to assist in retaining the drugs. The compositions afford retention of encapsulated agents, and reduced aggregation and fusion upon lyophilization and reconstitution, thereby providing useable compositions with extended shelf life. The enhanced protection from the lyophilization process is independent of osmotic potential. These liposomes maintain their size distribution and drug-encapsulation profiles over extended periods of time under pharmaceutically relevant conditions.

Methods to prepare the lyophilized liposome compositions thus may include a cryoprotectant external to the liposomes at a selected concentration wherein the liposome membrane prior to freezing and lyophilization is below its phase transition temperature $T_c$. Preferably, the liposomes are frozen at a temperature which is below the glass transition temperature ($T_g$) of the solution which comprises the liposomes with encapsulated drug as well as the extraliposomal medium which contains the cryoprotectant.

The invention is also directed, in other aspects, to methods of preparing lyophilized liposomes containing two or more therapeutic and/or diagnostic agents according to the embodiments set forth above, to methods of reconstituting said lyophilized compositions, and to methods of administering the reconstituted liposomes to animals, and to methods of treating animals affected by, susceptible to, or suspected of being affected by a disorder (e.g., cancer).

BRIEF DESCRIPTION OF THE DRAWINGS

FIG. 2 shows a particle size profile of reconstituted CPX-1 liposomes immediately after freezing, lyophilizing and reconstitution.

FIG. 3 shows a particle size profile of reconstituted CPX-1 liposomes 1 month after storage.

MODES FOR CARRYING OUT THE INVENTION

Figure 1:
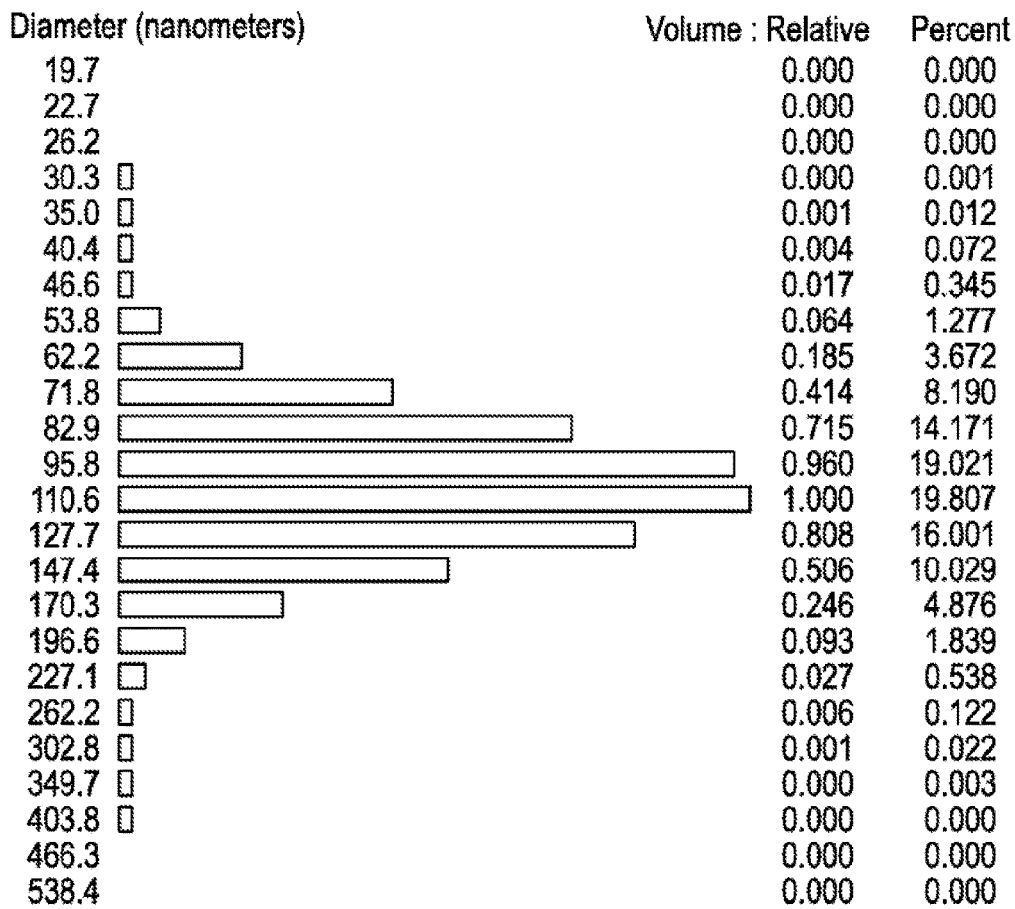
FIG. 1 shows a particle size profile of CPX-1 liposomes before freezing.

The invention provides, for the first time, lyophilized gel-phase liposomal compositions that contain two or more therapeutic and/or diagnostic agents such that the characteristics and properties of the reconstituted lyophilized composition essentially match those of the composition prior to lyophilization. These characteristics may include the mean diameter, size distribution, and contents of the liposomes. The content of the liposomes refers to the retention of the agents; in some embodiments, the ratio of the agents is retained as well.

Although the liposomes contain therapeutic and/or diagnostic agents, in the present application, "drugs" is sometimes used as a shorthand to designate these.

The gel-phase liposomes comprise one or more lipid bilayers enclosing an internal compartment. These liposomes can be bi-lamellar or unilamellar vesicles. Unilamellar liposomes (also known as unilamellar vesicles or "ULV") enclose a single internal aqueous compartment and are classified as either small unilamellar vesicles (SUV) or large unilamellar vesicles (LUV). LUV and SUV range in size from about 50 to 500 nm and 20 to 50 nm, respectively. Bilamellar liposomes have two lipid membranes wherein the inner membrane surrounds a single internal aqueous compartment and the second, larger outer membrane surrounds the inner membrane thus creating a second internal aqueous compartment.

Maintaining the size distribution of the gel-phase liposomes may be assessed experimentally by obtaining particle size profiles such as those set forth in FIGS. 1-4 herein. Size distribution determined by quasielastic light scattering is typically presented as a histogram showing the mean diameter of the liposomes. Significant size distribution measurements most commonly used in the art are D10, D90, D99 or a standard deviation or polydispersity index. "D99" values signify that 99% of the liposomes are less than a referenced size or more than a referenced size. This is particularly useful if, for example, it is important to exclude either an upper or lower size. For example, in certain embodiments it is desirable to ensure that no liposomes over 200 nm in mean diameter are present.

A specific example which has a D99 value of 178 nm is used to illustrate. A D99 value measuring 178 nm (as seen in Table 1 of Example 2) ensures that at least 99% of the liposome population is less than 178 nm. The D10 and D90 values for mean diameters, also commonly used, are those in which no more than 10% of the population is smaller than a minimum referenced size (i.e. D10) and for D90, where 90% of the population is at or less than an upper referenced size limit. For example, as seen in Batches 1 and 2, the D10 value is 68 nm such that no more than 10% of the liposome population is less than 68 nm. The D 90 value shows that 90% of the population is at or less than 135 or 137 nm for Batches 1 and 2, respectively. Maintaining the size distribution of the liposomes after lyophilization and reconstitution is defined herein as demonstrated by showing that the referent value of a selected D value changes by no more than 50%, 25%, 20%, 15%, 10%, 9%, 8%, 7%, 6% or 5% upon reconstitution compared to its value before freezing and/or lyophilization. The D values selected may be 99, 98, 94 and intervening integers to 90 or D10.

One characteristic of the lyophilized liposomes relates to the mean diameter of the liposomes in the composition. The mean diameter of a liposomal composition is maintained on reconstitution when the mean diameter of the liposomes does not increase more than 50%, 25%, on a volume weighted basis 20%, 15%, 10%, 9%, 8%, 7%, 6% or 5% after lyophilization and upon reconstitution based on the diameter before freezing. A concomitant value, such as a 10% increase in mean liposomal diameter coupled with a 10% increase in the referent for D90 (or other D value such as those listed above) is one measure to assure that the particle (e.g., liposomal) size distribution has not changed. The overall nature of the distribution can also be assessed preferably on a volume weighted basis, as shown in FIGS. 1-4.

In more detail, a composition of liposomes contains a range of sizes typically following a Gaussian curve. The mean diameter of the liposomes may increase by no more than about 30%, 25%, 20%, 15%, 10%, 9%, 8%, 7%, 6% or 5% from its original size upon reconstitution after freezing or lyophilization and reconstitution. For example, a sample of liposomes whose mean diameter is 90 nm would be considered to resist the effects of freezing and/or lyophilization if, upon reconstitution, the mean diameter is no more than 30% greater, i.e., about 117 nm. Size increases greater than these suggest that aggregation and fusion of the liposomes has occurred. A sufficiently sensitive measuring technique may be employed for measuring changes in size distribution or mean diameter so that changes of less than 10% can be measured.

Another criterion for preservation of integrity is retention of the encapsulated agents. Unlike mean diameter, size distribution and drug ratio, which are evaluated relative to pre-lyophilization values, drug retention is evaluated relative to total drug per se after reconstitution, i.e., based on the total drug in the lyophilized composition. The percentage of drug encapsulated inside the liposomes or the percentage of drug in the external medium outside of the liposomes (% "unencapsulated") are relative to the total amount of drug in the composition. In one embodiment, at least about 75% of the encapsulated agents is retained as encapsulated after lyophilization and upon reconstitution. At least about 85% of each may be retained as encapsulated and or at least about 90%, or 95%. This can similarly be measured by the amount of unencapsulated drug in the surrounding media which should not be more than 25%, 20%, 15%, 10% or 5% of the original amounts encapsulated upon reconstitution of the lyophilized liposomes.

The ratio of encapsulated therapeutic and/or diagnostic agents is maintained on reconstitution if the ratio does not vary by more than 20%, 10%, 9%, 8%, 7%, 6%, or 5% from the ratio in the pre-lyophilized composition itself. Ratios are expressed as molar ratios.

In one embodiment, the mean diameter of the liposomes after lyophilization and upon reconstitution of said liposomes will increase by no more than 25% as compared to said value measured prior to lyophilization. In another embodiment, the mean diameter of the liposomes after lyophilization and upon reconstitution of said liposomes changes by no more than 15% as compared to said value measured prior to lyophilization. In still other embodiments, the mean diameter of the liposomes after lyophilization and upon reconstitution of said liposomes changes by no more than 10%, 9%, 8%, 7%, 6%, or 5% as compared to said value measured prior to lyophilization.

In some embodiments, the percent of unencapsulated drug is no more than 25% of that originally encapsulated upon reconstitution of said liposomes. In other embodiments, the percent of unencapsulated drug is no more than 15% of that originally encapsulated upon reconstitution of said liposomes. In other embodiments, the percent of unencapsulated drug is no more than 10%, or is no more than 9%, 8%, 7%, 6% or 5% of that originally encapsulated upon reconstitution of said liposomes.

Stated another way, in some embodiments, the percent of the encapsulated drugs retained is no less than 75% upon reconstitution of said liposomes. In other embodiments, the percent of each encapsulated drug is no less than 85% or 90% or 95% upon reconstitution of said liposomes.

Combinations of these parameters are also included. For example, the mean diameter may increase no more than 25%, and the percentage of encapsulated drug be at least 90%, or the mean diameter may increase no more than 10% and the percentage of encapsulated drug at least 90%.

In some embodiments, the size distribution of the liposomes changes by no more than 25% after lyophilization and upon reconstitution of said liposomes as compared to prior to lyophilization. In other embodiments, the size distribution of the liposomes changes by no more than 15%, 10%, 9%, 8%, 7%, 6%, or 5% after lyophilization and upon reconstitution of said liposomes as compared to prior to lyophilization.

As noted above, various combinations of these parameters or criteria for successfully lyophilizing and reconstituting liposomes are contemplated—e.g., at least 85% encapsulated drugs combined with no more than 15% increase in mean diameter optionally combined with no more than 5% change in size distribution. Each of the possible combinations of these parameters is within the scope of the invention.

Gel-phase liposomes can be generated by conventional techniques, e.g., the ether injection method (Deamer, et al., Acad. Sci. (1978) 308:250), the surfactant method (Brunner, et al., Biochim. Biophys. Acta (1976) 455:322), the freeze-thaw method (Pick, et al., Arch. Biochim. Biophys. (1981) 212:186) the reverse-phase evaporation method (Szoka, et al., Biochim. Biophys. Acta. (1980) 601:559-571), the ultrasonic treatment method (Huang, et al., Biochemistry (1969) 8:344), the ethanol injection method (Kremer, et al., Biochemistry (1977) 16:3932), the extrusion method (Hope, et al., Biochim. Biophys. Acta (1985) 812:55-65) and the French press method (Barenholz, et al., FEBS Lett. (1979) 99:210).

These processes can be used in combination. Small unilamellar vesicles (SUVs) in particular can be prepared by the ultrasonic treatment method, the ethanol injection method and the French press method. Large unilamellar vesicles (LUVs) may be prepared by the ether injection method, the surfactant method, the freeze-thaw method, the reverse-phase evaporation method, the French press method or the extrusion method. Preferably, LUVs are prepared according to the extrusion method.

The lyophilization and reconstitution are conducted under conditions wherein the liposomes are in the gel phase. The gel-to-liquid transition temperature of the liposomes should therefore be greater than room temperature, i.e., about 20-30° C. and more preferably, at or above body temperature. Room temperatures may vary considerably, but it is important that the lyophilization process begin under conditions where the liposomes are in a gel state. In some embodiments, the $T_c$ is at least as high as body temperature (i.e., about 37° C.). In some embodiments, the liposomes are prepared at a temperature below the phase transition temperature in order to maintain the gel-like state. Any suitable internal medium may be employed. Typically, the internal medium is an aqueous medium. The internal medium contains substantially no cryoprotectant (i.e., less than 125 mM cryoprotectant). The internal medium may contain less than 100 mM cryoprotectant, or less than 50 mM cryoprotectant, or no cryoprotectant.

Liposome formulations which have suitable $T_c$ values may be "low cholesterol" liposomes, i.e., those prepared in the presence of, and containing an amount of cholesterol that is insufficient to significantly alter the phase transition characteristics of the liposome, i.e., typically 20 mol % or less cholesterol. Greater than 20 mol % of cholesterol broadens the range of temperatures at which phase transition occurs, with phase transition disappearing at higher cholesterol levels. A liposome having low cholesterol will have less than 20 mol % or less than 15 mol % cholesterol, or 10 mol % or 5 mol % or less cholesterol or be free of cholesterol. Such liposomes optimally require at least 1 mol % of a stabilizing agent such as PG or PI.

In those methods where cryoprotectant is used, the cryoprotectant preferably is present only in the external medium of the formulation. Typically, the cryoprotectants are disaccharides such as sucrose, maltose, trehalose and lactose. The cryoprotectant may be a disaccharide such as sucrose having a concentration that is about 100 mM to 500 mM or about 250-400 mM, or above 300 mM. The external medium may contain about 100 mM to 500 mM cryoprotectant and the internal medium contain less than 125 mM cryoprotectant or the external medium contains about 250 mM to 400 mM cryoprotectant and the internal medium contains less than 100 mM cryoprotectant or the external medium contains about 250 mM to 400 mM cryoprotectant and the internal medium contains less than 50 mM cryoprotectant or the external medium contains about 250 mM to 400 mM cryoprotectant and the internal medium contains no cryoprotectant. The cryoprotectant may be a saccharide, such as sucrose.

The gel-phase liposomal formulations can be lyophilized or freeze-dried using any appropriate protocol. The initial temperature of the lyophilization chamber is preferably below the glass transition temperature ($T_g$) of the solution which comprises the external medium as well as containing the liposomes with encapsulated drugs. For example, the liposomes may be frozen at a temperature below about −5° C., or below about −10° C., or below about −20° C., or below about −30° C., or below about −40° C. In some embodiments, when sucrose is used as the cryoprotectant solution, the initial temperature of the lyophilization chamber is less than −32° C. which is the $T_g$ of solution of sucrose. "$T_g$" includes the "glass transition temperature" and "glass phase transition temperature" which is the approximate midpoint temperature at which the unfrozen solution undergoes a transition from a soft, viscous gel to a hard and relatively brittle form.

The lyophilized liposomes may be stored at or below room temperature. Some exemplified embodiments have liposomes which are stored at or below 5° C. Some other exemplified embodiments have liposomes which are stored at 25° C. The lyophilized product remains stable (e.g., retains its relative particle size and maintains encapsulated drug) for at least about six months, or at least about nine months, or at least about one year, or at least about twenty-four to thirty-six months.

The entrapped agents are therapeutic or diagnostic agents, often anticancer agents. Remarkably, the contents and integrity of the gel-phase liposomal compositions are maintained even though the agents differ in their solubility characteristics with respect to aqueous and nonaqueous solvents. Using the approach of the invention, agents that differ in log partition coefficient (Log P) by as much as 1.0 may be successfully retained. Differences in log partition coefficient of 1.5 or 2.0 or 3.0 may be tolerated as well. One of the agents may be amphipathic while the other is water-soluble or one may be hydrophobic while the other is water-soluble. The Log P values are based on the partition coefficients between octanol and water—i.e., are the logarithm base 10 of the ratio of amount in octanol to the amount in water when the compound is subjected to phase separation.

The anticancer agents may include an anthracycline (for example, daunorubicin, doxorubicin, epirubicin or idarubicin). These agents are amphipathic. The anticancer agents may include a nucleoside analog for example, cytosine arabinoside, 5-FU or FUDR which are hydrophilic. Other anticancer agents include camptothecin or camptothecin derivative, such as irinotecan which are amphipathic. Both an anthracycline and a nucleoside analog are encapsulated in some cases or both a camptothecin or camptothecin derivative and a nucleoside analog are encapsulated. Encapsulation and/or loading of agents into liposomes may be carried out using any suitable loading techniques including passive and active loading. Important embodiments include those described in the above cited U.S. Pat. No. 7,850,990 and U.S. Pat. No. 8,022,279—i.e., combinations of irinotecan:floxuridine (FUDR) at 1:1 molar ratio and daunorubicin:cytarabine (AraC) at 1:5 molar ratio. Particular formulations of these drugs are designated CPX-1 and CPX-351, respectively.

The drugs are incorporated into the aqueous internal compartment(s) of the liposomes either by passive or active loading procedures or some combination thereof. In passive loading, the biologically active agent can be simply included in the preparation from which the liposomes are formed or, alternatively, the active agent can be added to the outside of preformed liposomes and loads passively down its concentration gradient into the liposomes. Optionally, unencapsulated material may be removed from the preparation by any suitable procedures. Alternatively, active loading procedures can be employed, such as ion gradients, ionophores, pH gradients and metal-based loading procedures based on metal complexation. One embodiment commonly employed for suitable drugs is loading via metal-based procedures.

The liposomes are about 80-500 nm in size. In one embodiment, the liposomes have a diameter of less than 300 nm, sometimes less than 200 nm. In one example, the nominal size of these liposomes is approximately 100 nm. In some embodiments, the liposome membrane is composed of distearoylphosphatidylcholine (DSPC), distearoylphosphatidylglycerol (DSPG) and cholesterol (CHOL). In some embodiments, the liposome membrane is composed of 50-80% DSPC, 1-20% DSPG and 1-20% CHOL. In other embodiments, the liposome membrane is composed of 50-80% DSPC or DPPC, 1-20% DSPG or distearoylphosphatidylinositol (DSPI), 1-20% CHOL and the liposomes contain less than 125 mM cryoprotectant in the intraliposomal medium. In some exemplified embodiments, the liposome membrane is composed of 50-80% DSPC or DPPC, 1-20% DSPG or DSPI, 1-20% CHOL and the liposomes contain less than 50 mM cryoprotectant in the intraliposomal medium. In other exemplified embodiments, the liposome membrane is composed of DSPC, DSPG and CHOL in about a 7:2:1 molar ratio and contain no cryoprotectant in the internal liposomal medium. In one instance, the liposomes are prepared by a water-in-oil derived liposome method and extruded liposomes are suspended in phosphate-buffered sucrose at pH 7.0. In another instance, the extruded liposomes are suspended in sucrose. In one embodiment, the extruded liposomes are suspended in 250-400 mM sucrose.

Any suitable means of encapsulating the drug combination in the liposomes can be employed. In a specific embodiment, irinotecan and floxuridine are co-loaded into DSPC/DSPG/CHOL (7/2/1) preformed liposomes whereby floxuridine is passively loaded into the liposomes and irinotecan is actively loaded at 50° C. using copper sulphate or copper gluconate in the internal medium. See co-owned U.S. Pat. Nos. 7,850,990 and 7,238,367 both of which are incorporated by reference. In another specific embodiment, cytarabine and daunorubicin are encapsulated in the liposome whereby the cytarabine is passively encapsulated into preformed liposomes and the daunorubicin is actively accumulated inside the liposomes at high trapping efficiencies using a copper gluconate/triethanolamine-based loading procedure. See, e.g., copending and co-owned PCT Applications WO05/102359 and WO07/076117A2 both of which are also incorporated by reference in their entirety.

The lyophilized compositions of the invention provide convenience in storage, preservation, and ease of shipping. These lyophilized compositions retain their characteristics over long periods of time.

For use, the compositions of the invention are reconstituted in a suitable pharmaceutical carrier or medium.

These formulations for use are prepared according to standard reconstitution techniques using a pharmaceutically acceptable carrier. Generally, normal saline will be employed as the pharmaceutically acceptable carrier. Other suitable carriers include, e.g., water, buffered water, dextrose, 0.4% sodium chloride, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The reconstituted formulations may be administered to animals, including humans, or other mammalian species, such as non-human primates, dogs, cats, cattle, horses, sheep, and the like, and may be used to treat a variety of diseases. Examples of medical uses of the compositions of the present invention include but are not limited to treating cancer, treating cardiovascular diseases such as hypertension, cardiac arrhythmia and restenosis, treating bacterial, fungal or parasitic infections, treating and/or preventing diseases through the use of the compositions of the present inventions as vaccines, treating inflammation or treating autoimmune diseases. For treatment of human ailments, a qualified physician will determine how the compositions of the present invention should be utilized with respect to dose, schedule and route of administration using established protocols. Such applications may also utilize dose escalation should bioactive agents encapsulated in liposomes and lipid carriers of the present invention exhibit reduced toxicity to healthy tissues of the subject.

The pharmaceutical compositions are typically administered parenterally, e.g., intravenously, but other routes may be employed. Dosage for the liposome formulations will depend on the ratio of drug to lipid and the administrating physician's opinion based on age, weight, and condition of the patient.

Overall, one process useful in the invention comprises lyophilizing a composition of liposomes wherein said liposomes comprise 20 mol % or less cholesterol and two or more active agents, and wherein the liposome membrane is below its phase transition temperature when at room temperature and in an external medium that contains a cryoprotectant; storing the lyophilized liposomes; and reconstituting the lyophilized liposomes in a predetermined aqueous volume. The liposomes are lyophilized at a temperature below about −5° C., or below about −10° C., and below about −20° C., or even below about −30° C. or −40° C., and can be stored at or below room temperature (about 23-25° C.).

In one embodiment, the liposome composition is comprised of 2-20% cholesterol, or at any intermediate value such as 10% cholesterol.

In one embodiment, the lyophilized composition comprises liposomes comprised of about 10% cholesterol, a disaccharide at a selected concentration in the external medium where reconstitution, performed at room temperature, is below the $T_c$, and wherein the cryoprotectant is unbound and present on the outside only of the liposomes.

In another embodiment, the lyophilized liposome composition comprising two or more encapsulated drugs upon reconstitution with a predetermined volume of aqueous medium, yields a liposome composition comprising: (a) liposomes containing 20 mol % or less cholesterol, (b) liposome sizes predominantly between about 80-500 nanometers, (c) liposome-entrapped agent(s) wherein the percent encapsulation of said agent(s) is not less than about 95%, 90%, 85%, 80% or 75%; and (d) between about 100 mM-500 mM cryoprotectant in the external liposomal medium. In some embodiments, between 250-400 mM cryoprotectant is present in the external liposomal medium. In some embodiments, about 9.5-10% cryoprotectant is present in the external liposomal medium.

In one embodiment, unilamellar or di-lamellar gel-phase liposomes comprising 20 mol % or less cholesterol, at least two drugs and at least about 300 mM sucrose on the outside of the liposomes are lyophilized and upon reconstitution at least about 90% of each of the encapsulated drugs is encapsulated and the mean liposome diameter changes by less than about 25%.

As used herein, "a" or "an" means "at least one" or "one or more," unless it is clear from the context that only a single referent is intended.

The following examples are provided solely to illustrate but not to limit the invention.

EXAMPLE 1

Lyophilization of CPX-1

Irinotecan and floxuridine 1:1 are co-encapsulated in DSPC/DSPG/Cholesterol (7:2:1 mol ratio) liposomes and designated CPX-1. Lyophilized CPX-1 resulted in stable drug-loaded liposomes, such that, there was minimal leakage of active pharmaceutical ingredients from the reconstituted dosage form. Irinotecan hydrochloride, used in CPX-1, has a predicted log partition coefficient (Log P) of 3.94. Floxuridine has a predicted Log P of −1.14.

Thermal analyses were generated for CPX-1 liposomal drug product using various lots to provide information on the glass transition temperature ($T_g$), change in heat capacity, and other exothermic events. The collapse temperature of CPX-1 liposomal drug product was determined by freeze dry microscope for two lots. These results were employed in determining the final lyophilization cycle.

The samples consisted of a bluish-green bulk aqueous suspension formulated with liposomes containing a 1:1 ratio of two active pharmaceutical ingredients, irinotecan hydrochloride and floxuridine. Samples were stored at −20° C. (or in some cases −80° C.) with ambient relative humidity, and thawed overnight in a refrigerator and mixed thoroughly prior to filling and lyophilization.

Cycle 1: Using a 20-mL Class A pipette, 20 cc of CPX-1, was filled into 60 cc glass molded vials. Twenty-four vials were loaded into a LyoStarII Tray Dryer with two product vials fitted with thermocouple probes to record product temperature and were freeze dried over four and one-half days. After backfilling the vials with nitrogen gas to a chamber pressure of about 720,000 mTorr, the vials were stoppered, removed from the Tray Dryer and labeled as Lot TP-CPX1-001-032405. Several of the lyophilized vials were then placed on accelerated stability at 25° C. and 40° C. with the remaining vials being stored at −20° C.

Cycle 2: Approximately 21-mL of CPX-1, were filled into 60 cc glass molded vials and 50 cc glass tubing vials, respectively. The vials were loaded into a LyoStarII™ Tray Dryer with one thermocouple probe in a product vial on the top shelf and one in a product vial on the bottom shelf. Upon completion of the lyophilization cycle, the vials were back-filled with nitrogen gas to a chamber pressure of about 720,000 mTorr, stoppered, removed from the Tray Dryer, and labeled as Lot TP-CPX1-002-041305T. Several of the lyophilized vials were then placed on accelerated stability at 25° C. and 40° C. with the remaining vials being stored at −20° C.

Cycle 3: The samples for lyophilization were prepared in a similar manner as for Cycle 2 except only filled into 50 cc glass tubing vials. The sealed vials were labeled as CPX-1 Drug Product, Lot TP-CPX1-003-051105T. Several of the lyophilized vials were then placed on accelerated stability at 25° C. and 40° C. with the remaining vials being stored at −20° C.

Cycle 4: The samples for lyophilization were prepared in a similar manner as for Cycle 2 except CPX-1, was filled into 50 cc glass tubing vials. The sealed, lyophilized vials were labeled as CPX-1 Drug Product, Lot TP-CPX1-004-051805T and stored for stability studies at −20° C., 5° C., 25° C., and 40° C.

Cycle 5: The samples for lyophilization were prepared in a similar manner as for Cycle 2 were filled into 50 cc glass tubing vials. The sealed, lyophilized vials were labeled as CPX-1 Drug Product TP-CPX1-005 062705T-300. The CPX-1 Liposomal Drug Product vials were stored in stability chambers at −20° C., 5° C., and 25° C.

First Lyophilization Cycle Run.

The primary goal for the first lyophilization cycle run (Cycle 1) was to determine if the formulated bulk CPX-1 liposomal drug product (CPX-1) could be successfully freeze dried with a gentle, two-step primary dry phase. The success of this lyophilization run was gauged by analyzing the drug product's temperature and pressure profiles and by visually inspecting the appearance of the lyophilized cakes.

The lyophilization product profile for cycle 1 showed that the bulk ice was removed during the −10° C. primary dry step. This was evident in that the product temperature slightly exceeded the shelf temperature. Also, the thermocouple pressure, which measures true pressure plus the partial pressure of water vapor, decreased toward that of the capacitance manometer pressure, or true pressure. In addition, the lyophilized drug product vials appeared dry with little, or no evidence of cake collapse. However, some analyte concentration or stratification was observed. To optimize the cycle, the thermal treatment phase and the primary drying steps were altered for the second run.

Second Lyophilization Cycle Run.

The second lyophilization run (cycle 2) was conducted using a similar gentle primary and secondary dry phases as cycle 1. To maximize the load of ice in the lyophilizer, vials filled with deionized water were loaded into unoccupied shelf space. The success of the lyophilization run was also gauged by the temperature and pressure profiles and by visually inspection of the lyophilized cakes.

The drug product in the 50 cc tubing vials appeared to freeze dry in a more homogenous manner even though the product temperature and pressure profiles for the 50 cc glass tubing vial and the 60 cc glass molded vial over the four and one-half day cycle were similar. About eight and one-half hours after reaching the secondary dry shelf temperature, the product temperature displays completion of the bulk ice sublimation by crossing over the ice barrier (i.e., the product temperature exceeds 0° C.). However, these vials were not sufficiently dried. The product temperature was below the shelf temperature at the end of the primary dry phase, and the difference between the thermocouple pressure and the capacitance manometer pressure was unchanged from the beginning of the run through the end of the secondary dry phase, which indicates the presence of substantial bulk ice in the vials.

Because the shelf temperatures employed in the primary dry phase failed to impart enough energy to drive the product sublimation rate toward completion, a third lyophilization cycle was developed to drive the primary drying phase to completion by using a shelf temperature and chamber pressure that increases ice sublimation, while not exceeding the collapse temperature.

Third Lyophilization Cycle Run.

Based on the results from cycle 2 and the thermal analyses, the shelf temperature and chamber pressure for cycle 3 were adjusted to facilitate primary drying, while maintaining product temperatures below the estimate collapse temperature of −20° C. To maximize the load of ice, the cycle was conducted under fully loaded run conditions.

The profile plot obtained for Cycle 3 showed that the initial primary dry shelf temperature, −20° C. at 100 mTorr pressure, did not drive the sublimation of bulk ice sufficiently in 40 hours under fully loaded run conditions. Also, the thermocouple pressure trace did not significantly decrease toward the capacitance manometer pressure until the end of the −10° C. primary dry phase due to the limited duration of this phase. However, the profile demonstrated that the −10° C. second primary dry shelf temperature and duration was able to maintain the product temperature below the collapse temperature of −20° C. until all of the bulk ice sublimated, which was evident in the rapid increase in product temperature to eventually exceed the shelf temperature at the end of the phase.

Fourth Lyophilization Cycle Run.

To finalize the shelf temperature(s) for the primary drying phase, the fourth lyophilization cycle (cycle 4) employed a shelf temperature of −10° C. for a longer duration with a 6-hour initial primary dry step at −20° C. under fully loaded run conditions.

Based on the lyophilization cycle profile and visual observation, the −20° C. shelf temperature for the initial primary dry phase appeared to have little benefit in drying the vials. The product temperature probes exceeded shelf temperature at −10° C. following a hold time of about 60 hours. The thermocouple pressure during the secondary drying phase indicated that the vials had relatively low residual moisture, since the product temperature profile closely matched that of the shelf temperature.

The encapsulation of drug substances, liposomal particle size, and average residual moisture was evaluated for vials of the lyophilized product. The Karl Fischer method employed recovered an average residual moisture content of 3.1%, which was not an overly dry liposomal product. Also, the analyses for particle size and percent encapsulation of irinotecan found that the lyophilized product was unchanged compared to the pre-lyophilized material. However, the percentage of unencapsulated floxuridine increased from 7.0% in the pre-lyophilized bulk to 8.6% in the lyophilized product when stored at −20° C. for 13 weeks. Also, after stressing the product for four weeks at 25° C., the percentage of unencapsulated floxuridine increased to 11.8%, which exceeded the tentative specification of less than 10% unencapsulated floxuridine for this drug product.

Fifth Lyophilization Cycle Run.

The goal of the fifth lyophilization cycle run (Cycle 5) was to decrease the shelf temperature for the secondary drying phase from +20° C. to +10° C. in order to minimize Floxuridine leakage while achieving a suitable residual moisture under fully loaded run conditions. The moisture content for this material was assessed during the secondary dry phase by periodically performing a pressure rise measurement.

The drug product profile for cycle 5 showed that the bulk ice was largely sublimated following 72 to 84 hours of primary drying at −10° C. Furthermore, the material appears to been dried sufficiently by employing a shelf temperature of +10° C. at 50 mTorr for 12 hours, based upon the pressure detector differences and the pressure rise studies.

To evaluate the suitability of this lyophilized material, the reconstitution time for lyophilized drug product vials from both cycles 4 and 5 were evaluated using 19 mL of water injected through the stoppers with an 18 gauge needle and a 30 cc syringe. The average reconstitution time was determined to be 40 and 93 seconds for cycles 4 and 5, respectively. Furthermore, the Karl Fischer results for cycle 5 recovered an average residual moisture of 3.2%, which was in good agreement with that of vials from cycle 4.

The encapsulation of the drug substances and liposomal particle size were also evaluated. For the cycle 5 lyophilized drug product, the percentage of unencapsulated irinotecan was 0.4% at −20° C. after 7 weeks of storage and 0.9% at 25° C. after 4 weeks of storage. The particle size for the lyophilized drug product increased only slightly after 8 weeks of storage at 5° C. compared to the drug product when stored at −20° C., but increased nearly 10 nm after only 4 weeks of storage at 25° C. Unsurprisingly, the percentage of unencapsulated floxuridine showed a similar trend to the particle size changes. The percentage of unencapsulated floxuridine was 5.5% at −20° C. after 7 weeks, 7.7% after 8 weeks at 5° C., and 18.7% at 25° C. after 4 weeks.

The fifth lyophilization cycle run, which employed a decreased shelf temperature during its secondary dry phase, succeeded in producing acceptable lyophilized CPX-1 liposomal drug product with increased retention of encapsulated product.

EXAMPLE 2

Particle Size Profile Over Time Remains Unchanged in Lyophilized Liposomes

Experiments were conducted in order to examine the impact of freezing, lyophilization and storage on the size distribution of dual-loaded CPX-1 and CPX-351 liposomes. CPX-351 is a formulation of daunorubicin and cytarabine at a mole ratio of 1:5 in liposomes that are distearoyl phosphocholine (DSPC):distearoyl phosphatidylglycerol (DSPG):and cholesterol (CHOL) at a mole ratio of 7:2:1. Daunorubicin has a predicted Log P of 1.68. Cytarabine has a predicted Log P of −2.17.

The particle size distribution of liposomes co-loaded was measured before and after freezing and lyophilization the liposomes as well as after one and six months of storing the lyophilized preparations.

CPX-1 liposomes were prepared with an external buffer of 300 mM sucrose, 20 mM phosphate, pH 7.0. Aliquots of 900 μl were added into 2 mL vials were placed into a metal pan (pre-cooled to −20° C.) and stored at −20° C. overnight. After freezing, the samples were moved to the lyophilizer (pre-cooled to −20° C.). The vacuum was applied and the shelf temperature was maintained at −20° C. for 7 hours and subsequently increased to −10° C. for approximately 16 hours. For a third temperature step, the shelf temperature was then raised further to 4° C. for the next 3 hours and then finished with a 3 hour dry at room temperature. Dried samples were hydrated with 1 mL of H$_2$O and readily dissolved the lyophilized cake. Samples were then analyzed using Dynamic Light Scattering (DLS).

Figure 4A:
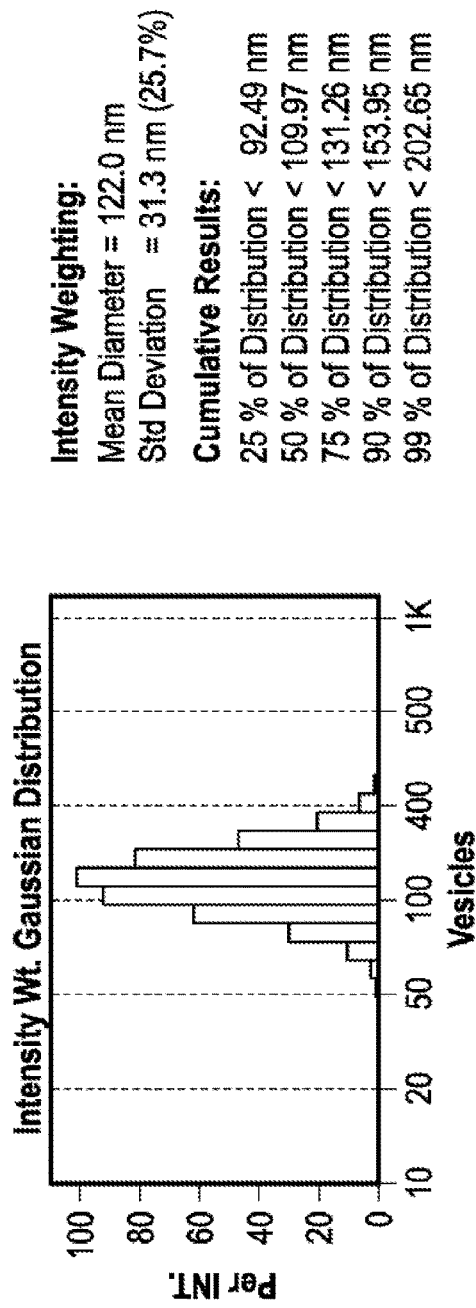
FIGS. 4A-4C show particle size profiles of reconstituted CPX-1 liposomes 6 months after storage.
Figure 4B:
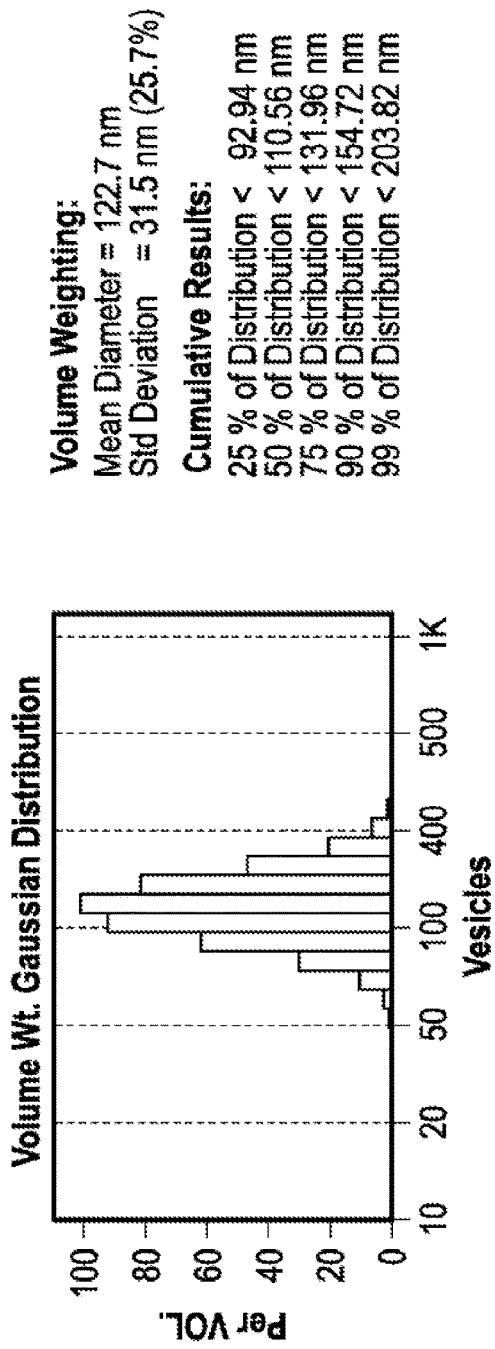
Figure 4C:
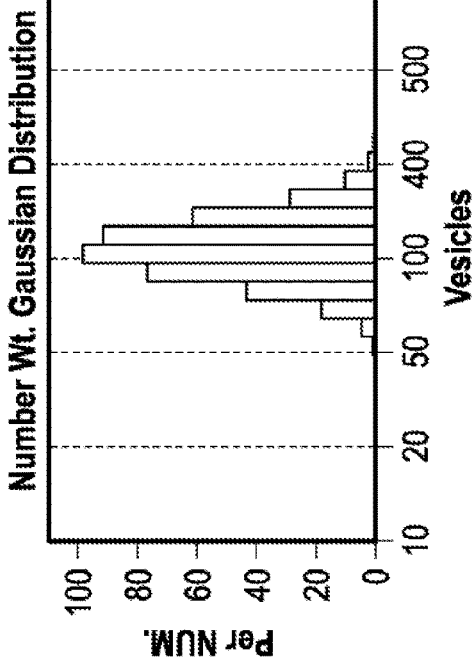

Pre-frozen CPX-1 liposomes showed a mean size diameter of 110 nm (FIG. 1). Liposome size immediately following lyophilization and rehydration were observed to be 116 nm (FIG. 2). Two samples of CPX-1 lyophilized liposomes were stored at 5° C. for one month or six months, and the liposome size of the rehydrated compositions was observed. The mean liposome size for each was 117 nm and 123 nm, respectively (FIGS. 3 and 4, respectively). FIGS. 1-3 show volume weighted distribution. FIG. 4B shows the comparable volume weighted distribution. Results of other less preferred algorithms are shown in FIGS. 4A and 4C. Unless otherwise specified, mean diameter refers to volume weighted distribution.

Experiments similar to those represented in FIGS. 1-4 were also carried out for CPX-351 liposomes.

As noted above, CPX-351 is a liposomal formulation of a fixed combination of the antineoplastic drugs cytarabine and daunorubicin hydrochloride. Liposomes are made using DSPC, DSPG and CHOL at a 7:2:1 mol ratio and with a copper gluconate—triethanolamine buffer, pH 7.4. The crude liposomes are extruded to bring the size distribution of the liposome particles where the mean liposome diameter must be between 80 nm and 110 nm with D99 not more than 200 nm (analysis by dynamic light scattering). Cytarabine is encapsulated by a passive loading mechanism. Daunorubicin is encapsulated by an active copper-mediated mechanism to achieve a cytarabine:daunorubicin molar ratio of 5:1. Any non-encapsulated drug substances are removed, and the bulk buffer is changed by diafiltration. Multiple volumes of 300 mM sucrose are exchanged to finalize the CPX-351 liposomes which are then run through a lyophilization optimization. Dried CPX-351 samples are reconstituted with 19 mL of H$_2$O and readily reform a liposomal dispersion. Samples are then analyzed using Dynamic Light Scattering (DLS).

Pre-lyophilized CPX-351 liposomes showed a mean size diameter of about 100 nm. Liposome size immediately following freezing and then lyophilization/rehydration were observed to be 99 nm and 100 nm, respectively for Batch 1 ("1C001" in Table 1 below). For a second batch, 1D002, CPX-351 liposome size immediately following freezing and then lyophilization/rehydration were observed to be 104 nm and 105 nm, respectively.

These results show that DSPC/DSPG low-cholesterol liposomes co-loaded with either irinotecan plus floxuridine or cytarabine plus daunorubicin effectively maintain their size distribution profiles upon freezing as well as lyophilizing and for prolonged periods of storage. The results here also show that these gel-phase liposomes prepared with low-cholesterol are resistant to aggregation and fusion which commonly results from freezing and lyophilizing particularly in the absence of high levels of cholesterol.

TABLE 1

Effects of Freezing and Lyophilization on CPX-351 Liposome Size

|  | CPX-351 Liposomes | | | |
|---|---|---|---|---|
|  | 1C001 (Batch 1) | | 1D002 (Batch 2) | |
|  | Frozen | Lyophilized/Rehydrated | Frozen | Lyophilized/Rehydrated |
| Mean diameter (nm) | 99 | 100 | 104 | 105 |
| D10 (nm) | 68 | 68 | 74 | 71 |
| D90 (nm) | 135 | 137 | 137 | 142 |
| D99 (nm) | 178 | 182 | 178 | 191 |

EXAMPLE 3

Percent Drug Encapsulation Over Time Remains Unchanged in Lyophilized Liposomes Experiments were conducted in order to examine the impact of freezing and/or lyophilization and storage on the extent of drug leakage from dual-loaded CPX-1 or CPX-351 liposomes.

The amount of encapsulated irinotecan and floxuridine in co-loaded CPX-1 liposomes was measured immediately after lyophilizing ("initial") as well as 6 and 9 months after storage at 5° C. Stability studies demonstrated the percent (%) encapsulation of irinotecan to be 99% immediately after lyophilization, 97% six months after storage and 97% nine months after storage (Table 2 below). Similarly, the percent encapsulation of floxuridine was 98% immediately after lyophilization and 95% at both six and nine months after storage at 5° C. (Table 3 below).

For CPX-351 liposomes, the effects of freezing and lyophilization on percent drug encapsulation were also studied. As seen in Table 4 below, the amount of encapsulated cytarabine in co-loaded CPX-351 liposomes was measured to be 100% immediately after freezing ("Frozen") and 98% after lyophilization ("Lyophilized") in two separate batches (1C001 and 1D002). The percent encapsulation of daunorubicin was 99% both immediately after freezing and lyophilization in both batches. Drug encapsulation is also stable when CPX-351 is stored at 5° C. or 25° C. (see Tables 5 and 6).

These results clearly demonstrate that both CPX-1 and CPX-351 gel-phase liposomes incorporating low amounts of cholesterol and a cryoprotectant in the external solution can effectively be frozen, dehydrated and reconstituted with minimal leakage of both encapsulated drugs.

TABLE 2

Percent Encapsulation of Irinotecan in Reconstituted CPX-1 Liposomes

|  | Stability Intervals | | |
|---|---|---|---|
| Test | Initial | 6 month | 9 month |
| Irinotecan - % Encapsulation | 99% | 97% | 97% |

TABLE 3

Percent Encapsulation of Floxuridine in Reconstituted CPX-1 Liposomes

|  | Stability Intervals | | |
|---|---|---|---|
| Test | Initial | 6 month | 9 month |
| Floxuridine - % Encapsulation | 98% | 95% | 95% |

TABLE 4

Percent Encapsulation of Cytarabine and daunorubicin in Reconstituted CPX-351 Liposomes

|  | CPX-351 Liposomes | | | |
|---|---|---|---|---|
|  | 1C001 | | 1D002 | |
|  | Frozen | Lyophilized | Frozen | Lyophilized |
| Cytarabine % encapsulation | 100 | 98 | 100 | 98 |
| Daunorubicin % encapsulation | 99 | 99 | 99 | 99 |

TABLE 5

CPX-351: Cytarabine Percent Encapsulation

|  | Time post-lyophilization | Stored at 5° C. | Stored at 25° C. |
|---|---|---|---|
| Batch 1C001 | Initial | 98 | 98 |
|  | 3 months | 98 | 98 |
|  | 6 months | 98 | 98 |
|  | 9 months | 98 | — |
| Batch 1D001 | Initial | 98 | 98 |
|  | 3 months | 98 | 99 |
|  | 6 months | 99 | 99 |
|  | 9 months | 98 | — |

TABLE 6

CPX-351: Daunorubicin Percent Encapsulation

|  | Time post-lyophilization | Stored at 5° C. | Stored at 25° C. |
|---|---|---|---|
| Batch 1C001 | Initial | 99 | 99 |
|  | 3 months | 99 | 99 |
|  | 6 months | 99 | 99 |
|  | 9 months | 99 | — |
| Batch 1D001 | Initial | 99 | 99 |
|  | 3 months | 99 | 99 |
|  | 6 months | 99 | 99 |
|  | 9 months | 99 | — |

The invention claimed is:

1. A lyophilized gel-phase liposomal composition, which composition comprises:
   (a) gel-phase liposomes that exhibit a melting phase temperature ($T_c$) of at least 37° C. and wherein the liposome membrane of said liposomes comprises no more than 20 mol % cholesterol and at least 1 mol % of a phosphatidylglycerol (PG) or a phosphatidylinositol (PI) or both; and wherein at least two therapeutic and/or diagnostic agents are stably associated with said liposomes wherein at least one of said agents is amphipathic or hydrophilic; and;
   (b) a cryoprotectant external to said liposomes; and wherein said liposomes contain less than 50 mM internal cryoprotectant, and wherein when said lyophilized gel-phase liposomal composition is reconstituted in a pharmaceutical carrier, the mean diameter of the liposomes is maintained as compared to said composition prior to lyophilization and said agents are substantially retained in the liposomes.

2. The composition of claim 1 wherein said liposome membrane comprises distearoylphosphatidylcholine (DSPC), distearoylphosphatidylglycerol (DSPG) and cholesterol (CHOL).

3. The composition of claim 1 wherein the liposome membrane comprises 50-80 mol % DSPC or dipalmitoyl phosphatidylcholine (DPPC), 1-20 mol % DSPG or distearoylphospatidylinositol (DSPI) and 1-20 mol % CHOL.

4. The composition of claim 3 wherein the liposome membrane comprises 50-80 mol % DSPC, 1-20 mol % DSPG and 1-20 mol % CHOL.

5. The composition of claim 4 wherein the liposome membrane has the components DSPC:DSPG:CHOL at 7:2:1 mol ratio.

6. The composition of claim 1 wherein the agents are antineoplastic agents.

7. The composition of claim 6 wherein the antineoplastic agents are daunorubicin and cytarabine, or are irinotecan and floxuridine.

8. The composition of claim 1 wherein said encapsulated agents are at a fixed ratio and wherein when said composition is reconstituted said ratio of the agents changes by no more than 25% as compared to said composition prior to lyophilization.

9. The composition of claim 1 wherein the mean diameter of the liposomes increases by no more than 25% after lyophilization and upon reconstitution of said liposomes as compared to said value measured prior to lyophilization.

10. The composition of claim 1 wherein said mean diameter is maintained for at least 6 months upon storage at from 5° C. to 25° C.

11. The composition of claim 1 wherein at least 75% of each agent is retained upon reconstitution of said liposomes.

12. The composition of claim 11 wherein said mean diameter is maintained for at least 6 months upon storage at from 5° C. to 25° C.

13. The composition of claim 1 wherein the size distribution of the liposomes changes by no more than 25% after lyophilization and upon reconstitution of said liposomes.

14. A method to prepare the composition of claim 1 which method comprises subjecting to lyophilization an aqueous medium comprising gel-phase liposomes wherein said liposomes exhibit a melting phase temperature ($T_c$) of at least 37° C. and the liposome membrane thereof comprises no more than 20 mol % cholesterol and comprises at least 1 mol % of a phosphatidylglycerol (PG) or a phosphatidylinositol (PI) or both; and said liposomes are stably associated with at least two therapeutic and/or diagnostic agents wherein at least one of said agents is amphipathic or hydrophilic and contain less than 50 mM internal cryoprotectant, in the presence of external protectants.

15. The method of claim 14 wherein said aqueous medium comprising said gel-phase liposomes is frozen at a temperature which is below the glass transition temperature ($T_g$) of said medium.

16. A method to prepare a pharmaceutical composition for administering therapeutic and/or diagnostic agents to a subject which method comprises reconstituting the liposomal composition of claim 1 in a pharmaceutical carrier to obtain a reconstituted composition.

17. The reconstituted composition of claim 16 for use in a method to administer therapeutic and/or diagnostic agents to an animal subject.

* * * * *